United States Patent

Woodard et al.

[11] Patent Number: 5,947,958
[45] Date of Patent: *Sep. 7, 1999

[54] RADIATION-TRANSMITTING SHEATH AND METHODS FOR ITS USE

[75] Inventors: Robert E. Woodard, Hayward; Julian N. Nikolchev, Portola Valley; Phillip M. Olsen, Sunnyvale, all of Calif.

[73] Assignee: Conceptus, Inc., San Carlos, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/528,654

[22] Filed: Sep. 14, 1995

[51] Int. Cl.⁶ .................................................. A61B 17/36
[52] U.S. Cl. ................................................ 606/15; 606/16
[58] Field of Search .................................. 606/10, 11, 12, 606/15, 16, 17; 604/96

[56] References Cited

U.S. PATENT DOCUMENTS

| | | |
|---|---|---|
| 300,525 | 6/1884 | Starr . |
| 951,285 | 3/1910 | Meyer . |
| 1,286,083 | 11/1918 | Pennington . |
| 2,843,112 | 7/1958 | Miller ........................................... 128/6 |
| 3,146,775 | 9/1964 | Moore et al. ................................. 128/6 |
| 4,612,938 | 9/1986 | Dietrich et al. ............................ 606/15 |
| 4,768,858 | 9/1988 | Hussein ................................. 606/15 X |
| 4,834,093 | 5/1989 | Littleford et al. . |
| 4,998,930 | 3/1991 | Lundahl ..................................... 606/15 |
| 5,125,925 | 6/1992 | Lundahl ..................................... 606/15 |
| 5,165,387 | 11/1992 | Woodson ..................................... 128/6 |
| 5,188,602 | 2/1993 | Nichols ..................................... 604/96 |
| 5,320,617 | 6/1994 | Leach ........................................ 606/15 |
| 5,354,293 | 10/1994 | Beyer et al. ............................. 606/15 |
| 5,354,923 | 10/1994 | Beyer et al. ............................. 606/15 |
| 5,394,863 | 3/1995 | Sanford et al. ............................ 128/3 |
| 5,458,595 | 10/1995 | Tadir et al. .............................. 606/15 |
| 5,478,338 | 12/1995 | Reynard ..................................... 606/15 |
| 5,478,339 | 12/1995 | Tadir et al. .............................. 606/15 |
| 5,505,725 | 4/1996 | Samson ..................................... 606/10 |
| 5,527,308 | 6/1996 | Anderson et al. ......................... 606/14 |

OTHER PUBLICATIONS

Wyss, P. et al. "Photomedicine of the endometrium: experimental concepts," *Human Reproduction*, 1995, vol. 10, No. 1 pp. 221–226.

*Primary Examiner*—Robert L. Nasser
*Attorney, Agent, or Firm*—Townsend and Townsend and Crew LLP

[57] ABSTRACT

A radiation transmitting sheath comprises a tubular body having a radiation guide extending axially therein. A coupler for attaching a radiation source is provided at the proximal end of the sheath. A dispersive tip for dispersing radiation from the radiation guide over a conical field is provided at the distal end of the sheath. Such sheaths are useful for providing illumination and endoscopic viewing methods and for providing sensitizing radiation in photodynamic therapy of body cavities.

23 Claims, 9 Drawing Sheets

RADIATION-TRANSMITTING SHEATH AND METHODS FOR ITS USE

BACKGROUND OF THE INVENTION

1. Field of the Invention

The present invention relates generally to medical instruments and methods for their use. More particularly, the present invention relates to the construction of a sheath having radiation-transmitting elements and use of such a sheath in methods for endoscopic viewing and for photodynamic therapy.

Sheaths are tubular devices commonly used for accessing body cavities and lumens for a wide variety of medical purposes. Of particular interest to the present invention, sheaths may be used for providing percutaneous access for fiberoptic viewing scopes in a number of endoscopic procedures, such as laparoscopy, hysteroscopy, arthroscopy, and the like. In such procedures, the sheath is typically introduced together with an internal stylet, where the stylet has a sharpened distal tip which permits percutaneous penetration. The stylet is then removed, and the desired viewing scope introduced through the central lumen of the sheath. Usually, the viewing scope will include glass lensing for viewing and fiber optics for illumination. In some cases, the viewing capability will be provided by a separate fiberoptic component. The need to provide both viewing and illumination components requires a larger viewing scope diameter than would otherwise be necessary for viewing alone. It would be desirable to be able to use a small diameter glass lens or fiber bundle viewing scopes, without the need to include additional fiberoptical capabilities for illumination.

Of further interest to the present invention, sheaths may also be used for introducing fiberoptic instruments for irradiating or illuminating the uterus and other body cavities in connection with photodynamic therapy. For example, sheaths may be used to first introduce a liquid solution having a radiation-activatable substance therein. After the solution is introduced, a fiberoptic device may be introduced through the central lumen of the sheath in order to irradiate the body cavity and induce the photodynamic therapy. It would be desirable to provide improved sheaths for this purpose which eliminate the need to separately introduce a radiation-transmitting device to illuminate or irradiate the body cavity.

For these reasons, it would be desirable to provide improved sheaths for accessing body cavities and lumens for the purposes of illumination, viewing, photodynamic therapy, and the like. In particular, it would be desirable to provide sheaths having the capability of transmitting light and other radiation wavelengths therethrough for illumination and photodynamic therapy. Such sheaths should incorporate radiation-dispersive tips which can substantially uniformly emanate radiation at the desired wavelength throughout a major portion of the body lumen or cavity. Such sheaths should also be of relatively simple construction, should be economic to fabricate, and should be compatible with conventional stylets in order to permit percutaneous introduction in a conventional manner.

2. Description of the Background Art

U.S. Pat. No. 4,768,858, discloses a hollow fiberoptic tube which can be introduced to a body lumen over a guidewire. The distal end of the tube is shown to be a flat annulus. A number of very early patents show speculums having internal illumination means. See, e.g., U.S. Pat. Nos. 300,525; 951,285; and 1,286,083. U.S. Pat. Nos. 2,843,112 and 5,167,387 describe endoscopes having self-illumination means. U.S. Pat. No. 3,146,775 describes a speculum having light transmitting fibers along its inner surface. U.S. Pat. No. 5,394,863 describes a cervical cup composed of a light transmitting material for illuminating the vaginal fornix during surgical procedures. U.S. Pat. No. 4,834,093 describes a catheter having a light transmitting fiber for focusing light to ablate lumenal obstructions. The use of photodynamic therapy for treating gynecological conditions is described in Wyss et al., (1995) *Hum. Reprod.* 10:221–226. A solid light fiber having a conical tip for directing light outward at a 90° angle is described in U.S. Pat. No. 5,354,293.

SUMMARY OF THE INVENTION

According to the present invention, a radiation transmitting sheath comprises a tubular member having a proximal end, a distal end, and at least one lumen extending therebetween. A radiation guide also extends axially from the proximal end to the distal end of the tubular member, and a coupler for attaching a radiation source is disposed on the proximal end of the radiation guide. A radiation dispersive tip is disposed at the distal end of the radiation guide. In this way, radiation, typically in the form of visible light, or near visible radiations such as ultraviolet and infrared light, may be transmitted through the sheath by connecting a radiation source to the coupler. The radiation emanating from the dispersive tip will be dispersed in a generally distal (axial) direction over a conical field having a conical angle of at least about 15°, typically ranging from 15° to 270°, usually from 15° to 180°, with a preferred range of from 30° to 180°. The ability to disburse light and other radiation over such a broad field is advantageous in both viewing methods, where a body lumen or cavity is to be endoscopically imaged, and in photodynamic therapy, where it is important to uniformly illuminate all surface areas of the body lumen or cavity without substantial shadowing or other discontinuities in the radiation dosage.

The radiation transmitting sheath will typically have a length in the range from 5 cm to 40 cm, usually in the range from 10 cm to 30 cm, and will typically have an outer diameter in the range from 2 mm to 15 mm, usually from 3 mm to 10 mm. The tubular member may be substantially rigid, particularly when it is to be used as a percutaneous sheath for the introduction of viewing means and/or other devices through its central lumen. Alternatively, the tubular member may be partially or fully flexible, particularly when it is being introduced through natural body orifices, such as through the cervix into the uterus for photodynamic therapy of the uterine endometrium. Optionally, a flexible tubular member may also have a steerable tip, e.g., selectively deflectable from up to 90° to 180°.

The radiation guide which extends through the tubular member may comprise a plurality of individual radiation transmissive fibers, typically arranged in a tubular bundle. Transmissive fibers could also be arranged in a braided pattern, thus providing additional structural support and allowing for a greater fiber packing density. Typically, such a tubular bundle will be embedded or encased in a protective structure, where the tubular bundle becomes a primary structural component of the tubular member of the sheath. Typically, the distal ends of the individual radiation transmitting fibers will be terminated at different angles in order to direct the emitted radiation over a range of angles from the distal tip of the radiation guide.

Depending on the wavelength of the radiation, the individual fibers may be composed of a variety of conventional materials, typically glass, quartz, and organic polymers, such as acrylates, particularly methylmethacrylates. The optical fibers, in turn, will be clad or imbedded in another material to provide the desired casing, such as a polyamide, polyvinylchloride, polypropylene, an adhesive, or the like.

The resulting tubular member, in turn, may be encased in a plastic, metal, or epoxy housing in order to provide the desired rigidity and to protect the device from damage.

As an alternative to the fiberoptic bundle, the radiation guide may be formed from a single tubular element having dimensions which generally correspond to those of the tubular member. Such a tubular fiberoptic element will be composed of the same materials as described above for the fiberoptic bundles, usually an acrylate. The single tubular element will also be clad or encased in another material, and will optionally have a mirrored external surface to provide the desired internal reflections. The distal end of the tubular radiation guide will typically be formed to have a spherical, irregular, or other desired geometry in order to provide the desired conical field of radiation projection.

The radiation transmitting sheath may include other components. Usually, the radiation transmitting sheath will include a proximal housing which provides the necessary connections for the stylet (in the case of percutaneously introduced sheaths), the radiation source, a balloon inflation connection (as described below), and the like. An expansible element may be provided on the exterior of the tubular member, particularly when the sheath is to be used for introduction through natural body orifices, such as when introduced through the cervix to access the uterus. The expansible element, typically in the form of an inflatable balloon, will be particularly useful when the sheath is being used to introduce a treatment solution into the uterus, as described in more detail below.

The present invention still further provides a sheath system comprising the sheath, generally as described above, in combination with the stylet having a sharpened distal tip. The stylet will have dimensions which permit the stylet to be selectively placed into and removed from the lumen of the tubular member so that the sharpened distal tip extends beyond the distal end of the tubular member. In this way, the assembly of the sheath and stylet may be self-introduced through tissue, typically through the abdomen in laparoscopic procedures.

A method according to the present invention for illuminating a body cavity or lumen comprises positioning a sheath so that a distal end of the sheath lies within the body cavity or lumen and a proximal end of the sheath lies externally to the body. A desired illuminating radiation wavelength, typically visible light, is directed to the proximal end of the sheath and is transmitted axially along or through the sheath to reach the distal end of the sheath. The illuminating radiation is disbursed from the distal end of the sheath over a distally disposed conical field having a conical angle ranging from 0° to 270°, usually from 15° to 180°, with a preferred range of from 20° to 45°. The method may further comprise introducing an instrument through a central lumen of the sheath, where the instrument is typically a viewing scope. It will be appreciated that by providing illumination in the sheath, it may not be necessary to provide fiberoptic illumination capability in the viewing scope. Thus, viewing scopes having smaller dimensions may be utilized.

According to a further aspect of the method of the present invention, a body cavity or lumen may be treated by first positioning a sheath so that a distal end of the sheath lies within the body cavity or lumen and a proximal end of the sheath lies externally to the body. A solution containing a radiation sensitive substance, typically a photodynamic material such as a porphyrin, is introduced through the sheath to the body cavity or lumen. Before the solution is introduced, the cavity or lumen will usually be sealed by expanding an occluding element, typically an inflatable balloon, within an access orifice or passage to the lumen or cavity. Radiation having a wavelength selected to activate the radiation sensitive substance is then directed to the proximal end of the sheath so that it passes through the sheath into the body cavity or lumen. The radiation is disbursed from the distal end of the sheath to activate the radiation sensitive substance within the body cavity or lumen. An exemplary method comprises treatment of the uterine endometrium in order to achieve partial or full ablation thereof. Such treatment may be useful as a therapy for certain tumorous conditions, such as myomas, or for the treatment of excessive uterine bleeding.

DETAILED DESCRIPTION OF THE SPECIFIC EMBODIMENTS

Figure 1:
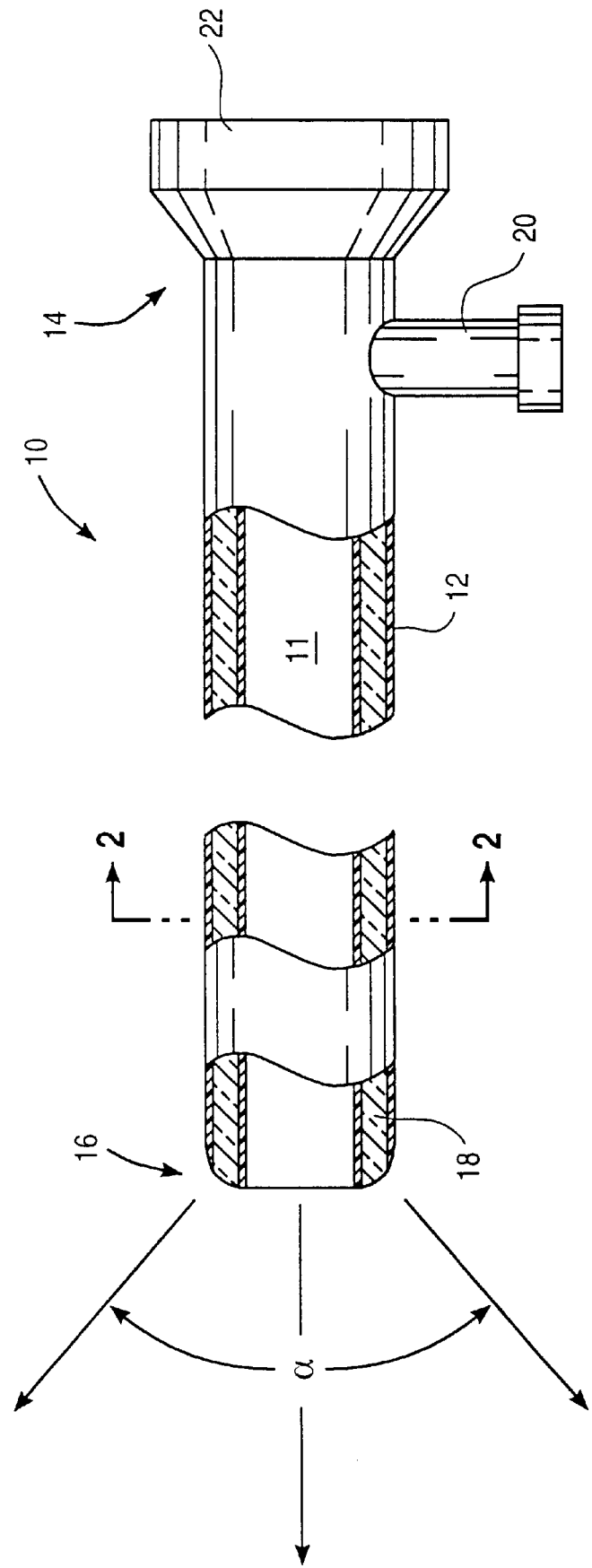
FIG. 1 illustrates a radiation transmitting sheath constructed in accordance with the principle of the present invention, with portions broken away.

A radiation transmitting sheath according to the present invention will comprise a tubular member, a radiation guide extending through the tubular member, a coupler for attaching a radiation source to the radiation guide, and a radiation dispersive tip at the distal end of the radiation guide. As used herein, the tubular member will be a rigid, flexible, or semi-flexible structure or assembly having a proximal end and a distal end. Usually, the diameter of the tubular member will be uniform over its entire length, although this is not essential. The outer diameter will typically be in the range from 2 to 15 mm, usually from 3 to 10 mm, with an inner diameter in the range from 1 to 14 mm, usually from 2 to 9 mm. The tubular member will typically be formed together with or as part of the radiation guide, as discussed in more detail hereinbelow. In some cases, however, it may be possible to form a separate tubular member where the radiation guide is attached over an inner or outer surface thereof.

The radiation guide will typically be formed from one or more optical fibers according to well known principles. The optical fiber(s) will be composed of materials conventionally used for optical fibers and wave guides, such as glass, quartz, and organic polymers, particularly polyacrylates, and more particularly methylemethacrylates. Other suitable polymers include polystyrene. The optical fibers will be externally clad and/or have a reflective coating placed over their exterior surfaces in order to provide for the desired internal reflections which permit light and other radiation transmission. The dimensions of the optical fibers will depend on the number employed in a particular device. In the case of fiberoptic bundles, the individual fiberoptic members will typically have a diameter in the range from 10 μm to 200 μm, usually from 20 μm to 70 μm with a range of sizes employed to achieve a more efficient packing configuration. In the case of a single, tubular optical fiber, the outer and inner diameters correspond generally to those of the tubular member itself.

A coupler for attaching a radiation source, typically a light source, to the proximal end of the radiation guide will be located at the proximal end of the tubular member. In the case of optical fiber bundles, the coupler may simply be the bundle itself which is cut and polished to provide an interface to the radiation source. In the case of a single optical fiber (which will typically not be flexible and cannot be bent to form the coupler, as with the fiberoptic bundle), a conventional coupling collar or other device will be provided.

The distal end of the radiation guide will typically be formed to provide for the desired radiation dispersive pattern. For example, in the case of both fiberoptic bundles and a single tubular fiberoptic element, the distal end of the radiation guide could be formed into a partial sphere, such as a generally hemispherical surface. The hemispherical surface will emit radiation substantially uniformly over a conical volume, as described in more detail below. Alternatively, the distal end of the radiation guide can be formed with a plurality of facets which direct discrete beams in a plurality of directions. A sufficient number of facets can be provided in order to uniformly distribute radiation substantially over the desired conical pattern. Such facets may be formed by controlling the termination angle of the individual fibers within a fiberoptic bundle. Alteratively, the facets could be formed in the distal end of a single, tubular fiberoptic element. It will be appreciated, however, that other dispersive elements, including lens systems, refraction gradients, and the like, could also be provided for dispersing light over the desired conical pattern.

Referring now to FIG. 1, a radiation transmitting sheath 10 comprises a tubular member 12 having a proximal end 14 and a distal end 16. A single, tubular radiation guide 18 is annularly disposed in the tubular member 12, and terminates at its distal end in a quarter-circular section. This way, radiation emanating from the distal end 16 will cover a desired conical field having a conical angle α, as illustrated. The sheath 10 further includes a coupler 20 which allows connection of the radiation guide 18 to an external radiation source, typically a visible light source, more typically a laser light source, such as Coherent, Inc., Palo Alto, Calif.; Laserscope, San Jose, Calif.; and Melles Griot, Laser Division, Carlsbad, Calif. The sheath further includes an end-connector 22 which permits coupling of a conventional endoscopic viewing device, as will be described in more detail below.

Figure 2A:
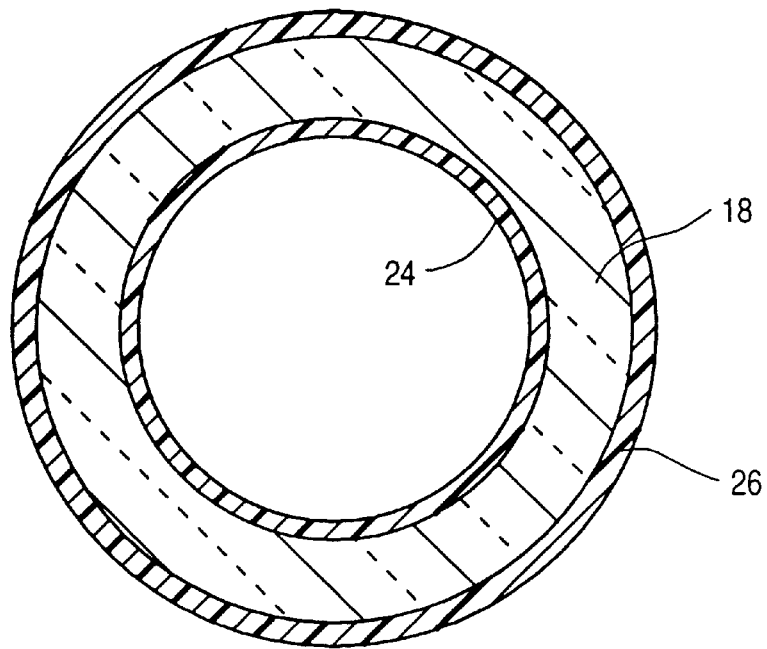
FIG. 2A is a cross-section view taken along line 2—2 of FIG. 1.

In the sheath embodiment of FIG. 1, the radiation guide comprises a single tubular optical fiber 18, as best illustrated in FIG. 2A. The tubular optical fiber 18 is clad or coated with an internal layer 24 and an external layer 26. The cladding or layers 24 and 26 will typically be composed of polymeric materials, for example, polycarbonates, polyvinylchlorides, polypropylenes, or the like, which have been colored to provide for the desired internal reflection within the radiation guide. The thickness of layers 24 and 26 is not critical, typically being in the range from 0.1 mm to 1 mm, more typically in the range from 0.3 mm to 0.5 mm. The thickness of the radiation guide 18, in turn, is typically in the range from 0.01 mm to 3 mm, more typically from 0.25 mm to 1 mm.

Figure 2B:
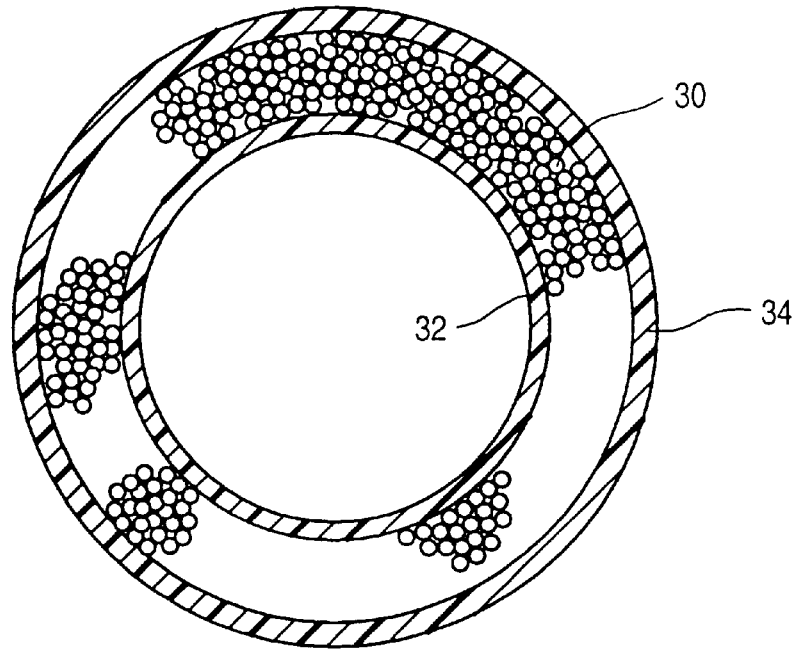
FIG. 2B is an alternative embodiment of the cross-sectional view taken along line 2—2 of FIG. 1.

In an alternative embodiment, the radiation guide 18 may be replaced by a plurality of individual optical fibers, as illustrated in FIG. 2B. The optical fiber are preferably formed into one or more annular layers (with a plurality of layers being shown), optionally arranged as a tubular bundle 30 which is encased between inner and outer layers 32 and 34. The layers 32 and 34 may be discrete, e.g., preformed and later attached over the optical fiber bundle 30. Alternatively, either or both of the layers 32 and 34 may be formed by impregnating the optical fiber bundle 30. A wide variety of specific fabrication methods would be available and may be practiced by anyone skilled in the art. In some cases, it may be desirable to braid the individual fibers so that they are structurally self-supporting, eliminating the need for layers 32 and 34.

Figure 3:
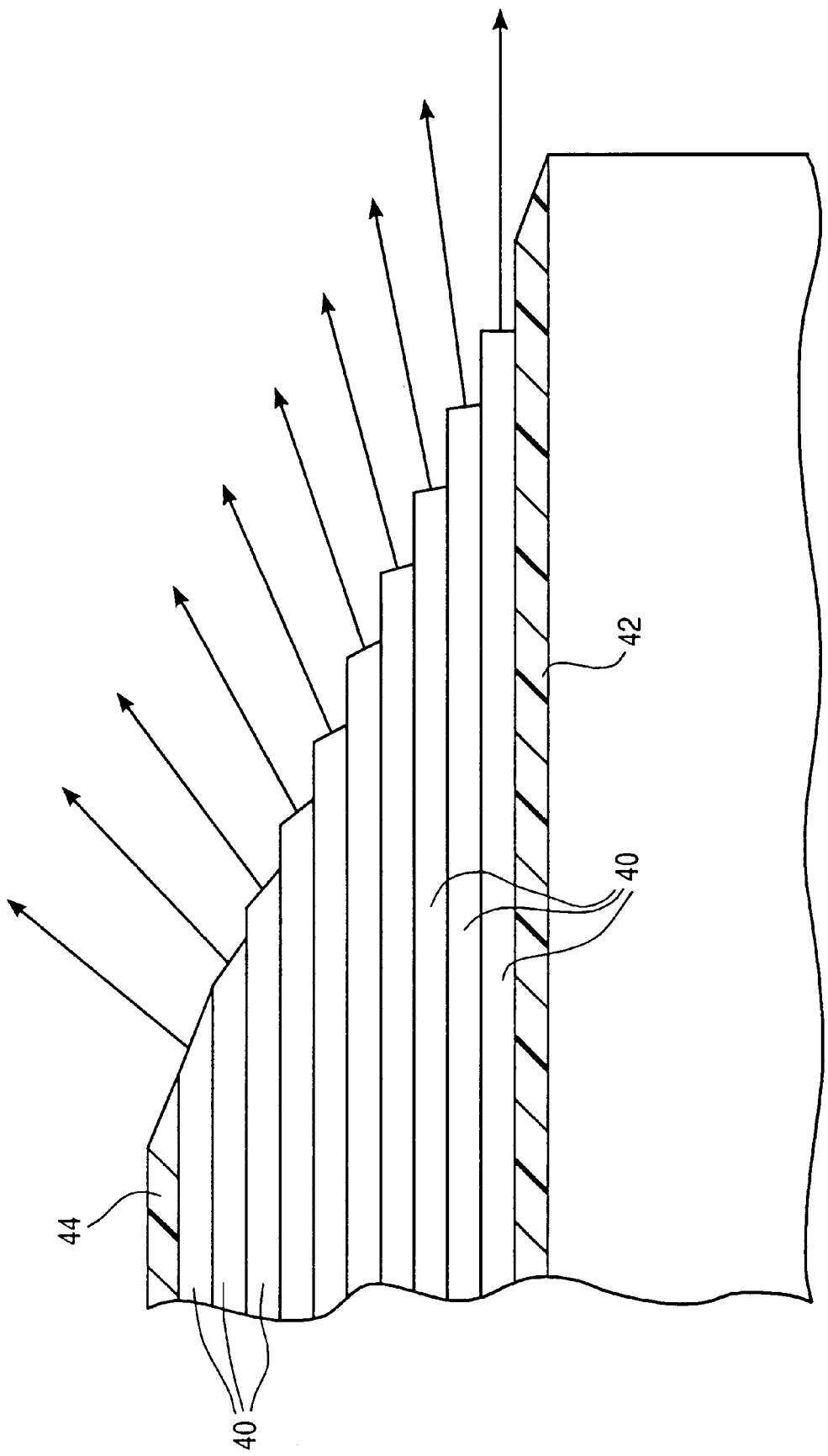
FIG. 3 illustrates an alternative light-disbursing construction for the distal tip of the sheath of FIG. 1.

As an alternative to the rounded distal dispersive tip of FIG. 1, the dispersive tip may be formed as a plurality of individual facets arranged to direct individual beams in different directions, as illustrated in FIG. 3. In FIG. 3, a plurality of individual optical fibers 40 are encased between an inner layer 42 and an outer layer 44. The distal ends of each individual optical fiber are terminated at slightly different angles so that the light is directed from each fiber along a slightly different path, as indicated by the arrows. It will be appreciated that by providing a sufficient number of optical fibers, typically from 100 to 500, preferably from 150 to 300, the radiation emanating from the distal tip will be dispersed substantially uniformly over the desired conical field.

Figure 4B:
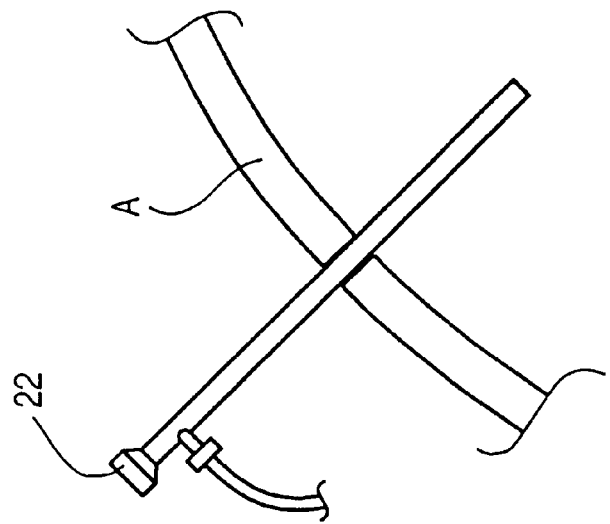
FIGS. 4A–4C illustrate use of the device of FIG. 1 for laparoscopically introducing a viewing scope into a patient's abdominal cavity.
Figure 4A:
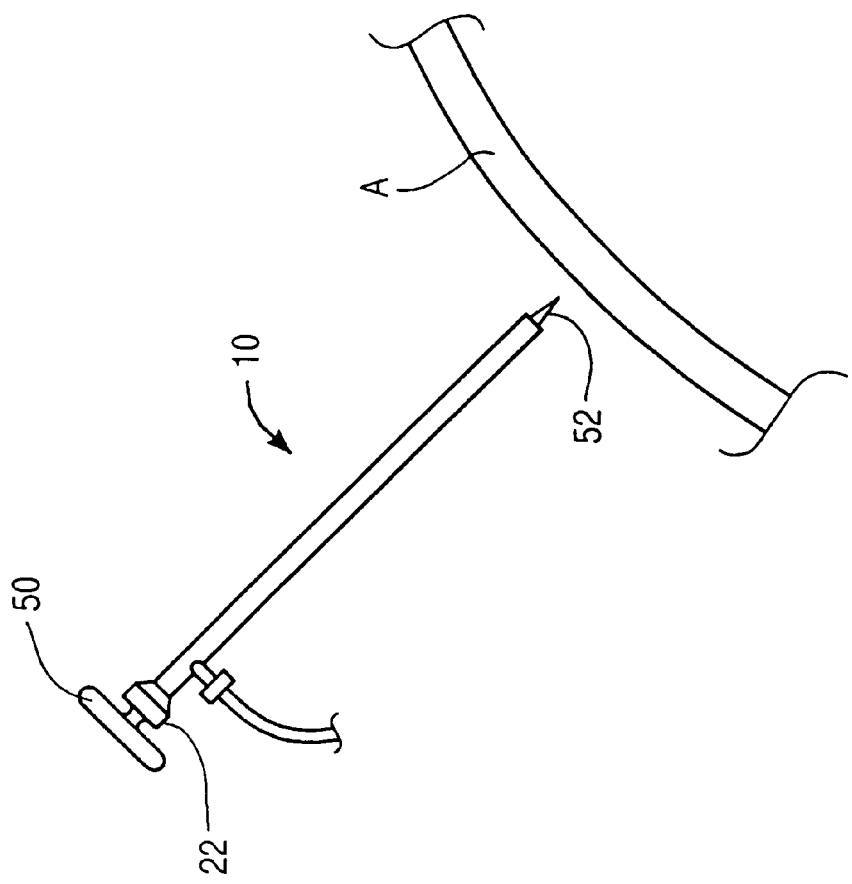
Figure 4C:
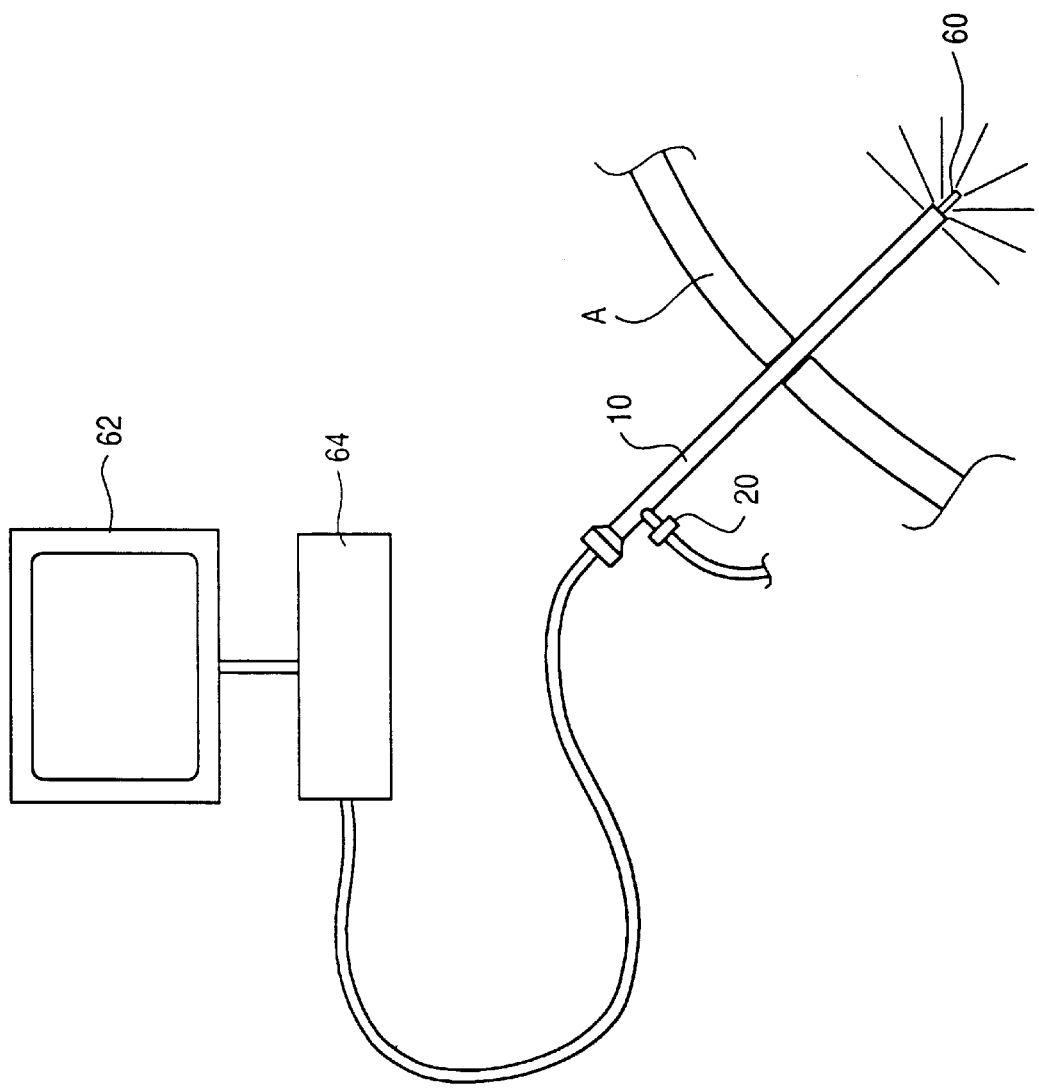

Referring now to FIGS. 4A to 4C, use of the sheath 10 for percutaneously introducing a viewing scope, typically a laparoscope, through a patient's abdominal wall A is illustrated. Initially, a stylet 50 having a sharpened distal tip 52 is placed in the central lumen 11 of the sheath 10. The sheath and stylet may thus be introduced percutaneously by advancing the sharpened distal tip through the abdominal wall in a generally conventional manner. The stylet is then withdrawn, as illustrated in FIG. 4B, and a viewing scope attached through the end connector 22, as illustrated in FIG. 4C. The viewing scope 60 extends distally from the sheath 10, and the abdominal cavity may be illuminated by directing visible light through the connector 20. The abdominal cavity may be viewed on a conventional video monitor 62 through convention laparoscopic imaging equipment 64.

Figure 5A:
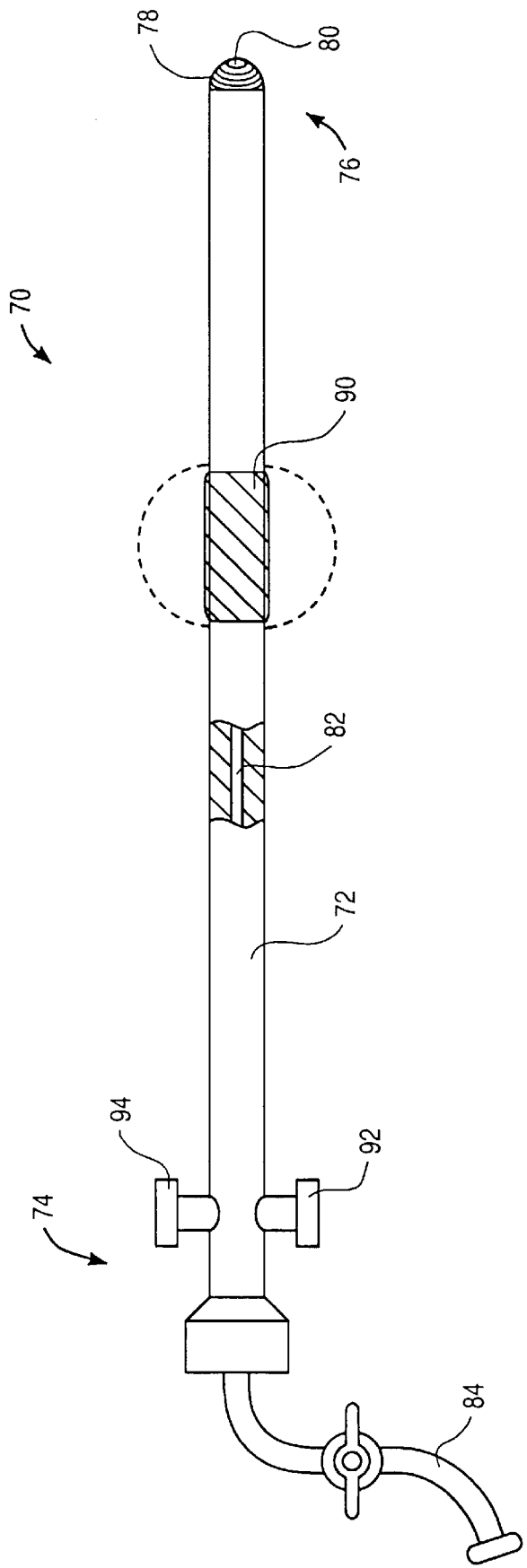
FIGS. 5A and 5B illustrate alternative constructions of the sheath of the present invention, which sheath is intended particularly for photodynamic radiation therapy of the uterus.

An alternative embodiment of the sheath of the present invention, shown as sheath 70 in FIG. 5A, comprises a tubular member 72 having a proximal end 74 and a distal end 76. A radiation dispersive tip 78 is disposed at the distal end of the member 72 and may comprise any of the dispersive structures discussed above. A distal port 80 is also located at the distal end of the tubular member 72 and is connected via an internal lumen 82 to a fluid connector 84 at the proximal end. This way, a treatment solution may be introduced through the connector 84 and discharged from the distal port 80 in order to effect photodynamic therapy, as described below.

An occluding balloon 90 is disposed on the tubular member 72, typically being composed of an elastomeric material and having an inflated diameter (as shown in broken line) in the range from 5 mm to 30 mm. The balloon 90 will be disposed proximally of the distal end of the tubular member 72 by a distance in the range from 1 cm to 10 cm. This distance is particularly suitable for sealing of the cervix and treatment of the endometrium of the uterus, as described below. A first connector 92 is provided for coupling an internal radiation guide to the dispersive tip 78. A second connector 94 is provided for connecting a source of inflation medium to the balloon 90.

Figure 5B:
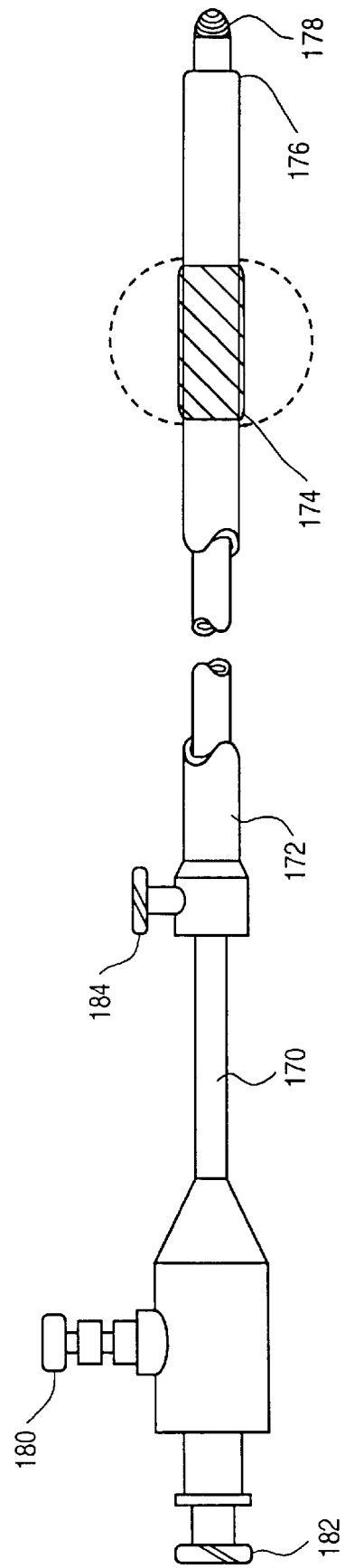

Alternatively, a balloon could be provided separately as a coaxial sleeve or sheath disposed over the cannula of the present invention. In this way, the cannula could be axially positioned within the balloon sleeve to selectively place the distal end of the cannula. See FIG. 5B where a sheath 170 is disposed in a coaxial sleeve 172 having an inflatable balloon 174 near its distal end 176. The sheath 170 includes a radiation dispersive tip 178 and a coupling member 180 for attaching the tip to a suitable radiation source. A luer connector 182 is provided for introducing fluid and/or attaching a suitable fiberoptic scope through the sheath 170. A separate inflation connector 184 is provided on a proximal end of the coaxial sleeve 172.

Figure 6A:
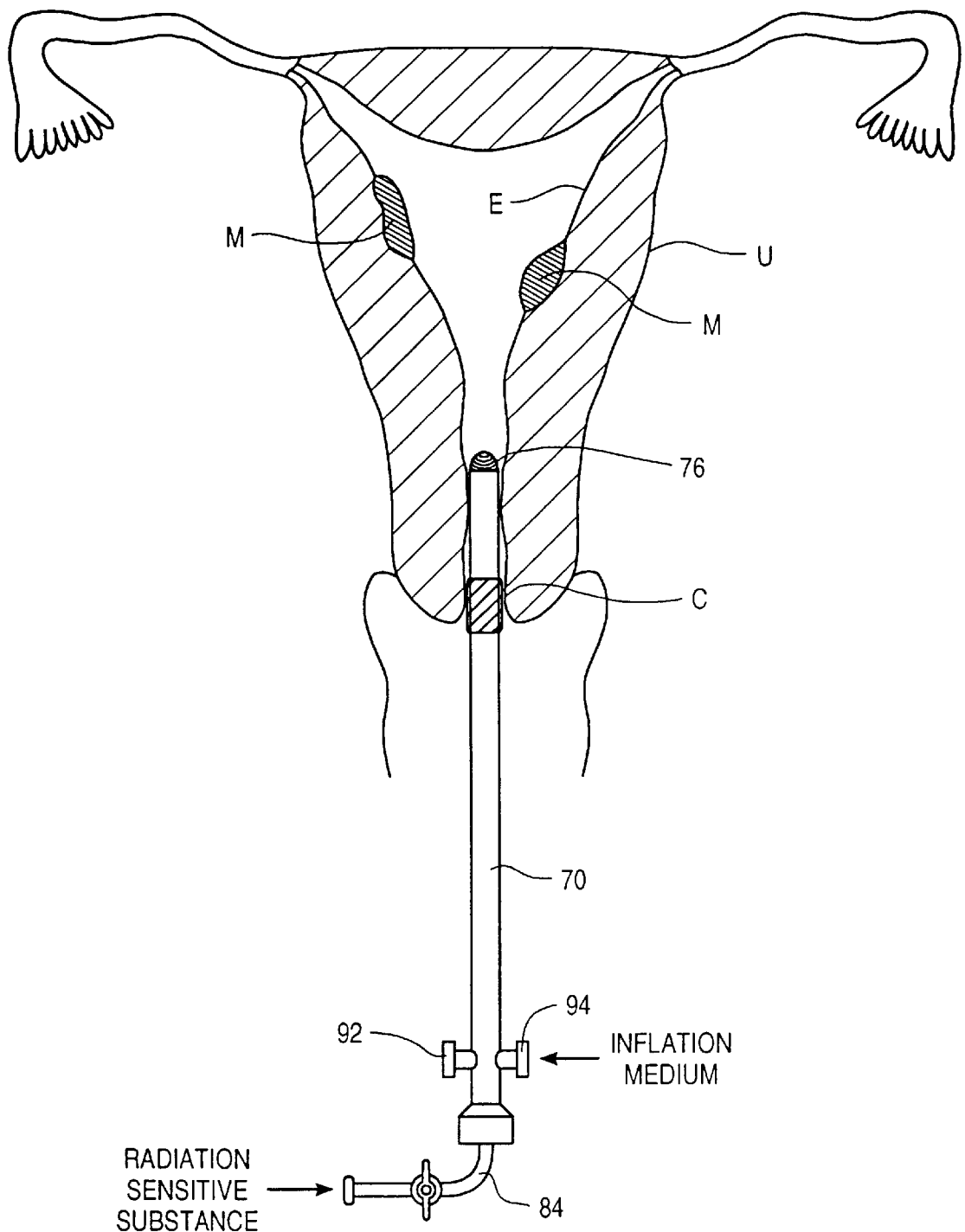
FIGS. 6A–6B illustrate the use of the device of FIG. 5 for endometrial ablation of the uterus.
Figure 6B:
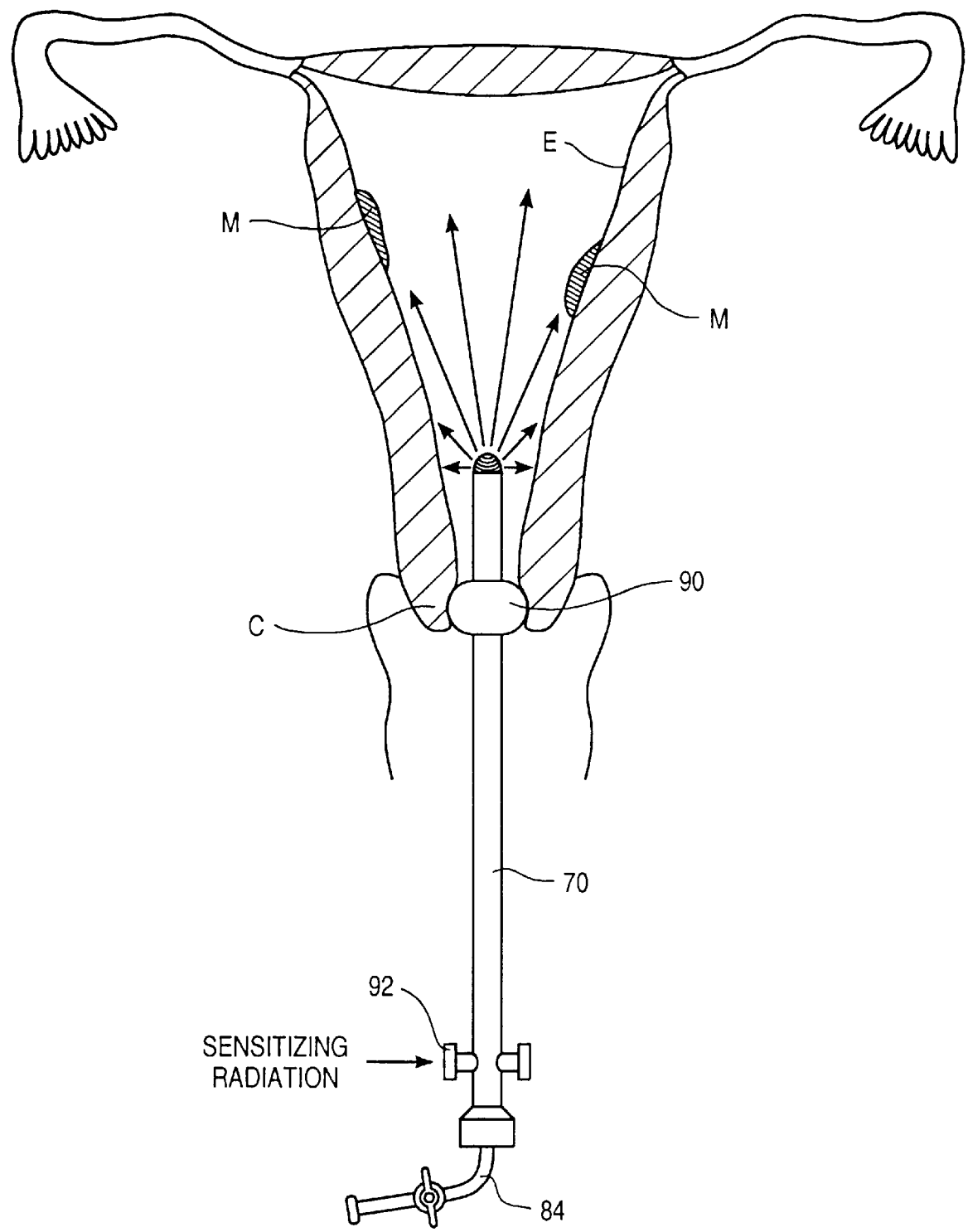

Referring now to FIGS. 6A and 6B, ablation of the endometrium E of a patient uterus U will be described. The sheath 70 is introduced through the cervix C so that its proximal end 76 lies within the uterus, as illustrated in FIG. 6A. An inflation medium is then directed through connector 94, to inflate balloon 90, as shown in FIG. 6B. After balloon 90 inflation, a treatment solution comprising a radiation sensitive substance, typically a porphyrin, is introduced through the connector 84 until it fills and slightly distends the uterine cavity. Sensitizing radiation, typically light, may then be directed through the sheath 70 by connecting a suitable light source to the first connector 92. Light will be radiated from the distal end of the sheath in all directions, as shown by arrows in FIG. 6B. The combination of light sensitive material and dispersed light will cause endometrial ablation. Such ablation is useful for treatment of a variety of conditions, including the treatment of myomas M which may be present on the endometrium.

Although the foregoing invention has been described in some detail by way of illustration and example, for purposes of clarity of understanding, it will be obvious that certain changes and modifications may be practiced within the scope of the appended claims.

What is claimed is:

1. A radiation transmitting sheath comprising:
   a tubular member having a proximal end, a distal end, a tubular wall, and a central lumen extending therethrough;
   a tubular radiation guide extending axially from the proximal end to the distal end thereof within the tubular wall of the tubular member; and
   a coupler for attaching a radiation source to the proximal end of the radiation guide;
   wherein the distal end of the radiation guide is shaped to disperse radiation from the guide over a distally disposed diverging conical field having a conical angle of at least 15°.

2. A radiation transmitting sheath as in claim 1, wherein the distal end of the radiation guide is shaped to disperse radiation over a conical field having a conical angle in the range from 15° to 270°.

3. A radiation transmitting sheath as in claim 2, wherein the distal end of the radiation guide is shaped to disperse radiation over a conical field having a conical angle in the range from 30° to 180°.

4. A radiation transmitting sheath as in claim 1, wherein the tubular member has a length in the range from 5 cm to 40 cm and an outer diameter in the range from 2 mm to 15 mm.

5. A radiation transmitting sheath as in claim 1, wherein the tubular member is substantially rigid.

6. A radiation transmitting sheath as in claim 1, wherein the radiation guide comprises a plurality of individual radiation transmissive fibers arranged in a tubular bundle.

7. A radiation transmitting sheath as in claim 6, wherein the fibers are braided.

8. A radiation transmitting sheath as in claim 6, wherein the individual radiation transmitting fibers are embedded or encased in a protective structure to form the tubular member.

9. A radiation transmitting sheath as in claim 6, wherein the distal ends of the individual radiation transmitting fibers are terminated at different angles to form the radiation dispersive tip.

10. A radiation transmitting sheath as in claim 1, wherein the radiation guide consists of a single tubular element.

11. A radiation transmitting sheath as in claim 10, wherein the tubular element is clad on its inner and outer surfaces.

12. A radiation transmitting sheath as in claim 10, wherein the distal end of the tubular element is formed to have a spherical surface to disperse radiation in the desired pattern.

13. A radiation transmitting sheath as in claim 1, further comprising an expansible element on the tubular member, wherein the expansible member is adapted to occlude a body cavity or lumen when the sheath is located therein whereby a fluid may be delivered to the body cavity or lumen without leakage past the expansible member.

14. A radiation transmitting sheath as in claim 13, wherein the expansible member is an elastic balloon connected to a second lumen within the tubular member.

15. A sheath as in claim 13, further comprising a coaxial sleeve slidably received over the tubular member, wherein the expansive element is disposed on the coaxial sleeve.

16. A sheath system comprising:
    a sheath as in claim 1; and
    a stylet having a sharpened distal tip, wherein the stylet has dimensions which permit it to be removably placed in the lumen of the tubular member so that the sharpened distal tip extends beyond the distal end of the tubular member.

17. A method for illuminating a body cavity, said method comprising:
    positioning a sheath having a cylindrical wall comprising a tubular radiation guide so that a distal end of the sheath lies within the body cavity and a proximal end of the sheath lies externally to the body;
    directing illuminating radiation to the proximal end of the sheath, wherein the illuminating radiation is transmitted axially through the tubular radiation guide to the distal end of the sheath; and
    dispersing the illuminating radiation from the distal end of the sheath over a distally disposed diverging conical field having a conical angle of at least 15°.

18. A method as in claim 17, further comprising introducing an instrument through a central lumen of the sheath.

19. A method as in claim 18, wherein the instrument is a viewing scope and the method further comprises viewing the body cavity under the dispersed illuminating radiation.

20. A method as in claim 17, further comprising viewing the body cavity via a viewing scope introduced to the cavity by other than the sheath.

21. A method as in claim 17, wherein the illuminating radiation comprises visible infrared, or ultraviolet light.

22. A method as in claim 17, wherein the sheath is positioned percutaneously by placing a removable stylet within a central lumen of the sheath, penetrating the sheath and stylet through tissue to the body cavity, and removing the stylet to leave the central lumen as a working channel.

23. A method as in claim 22, wherein the body cavity is the peritoneum, further comprising the step of insufflating the peritoneum before or after penetrating the sheath and stylet.

* * * * *